US006725180B2

(12) United States Patent  
Mayer et al.

(10) Patent No.: US 6,725,180 B2
(45) Date of Patent: Apr. 20, 2004

(54) ENVIRONMENTAL MONITORING SYSTEM (75) Inventors: John Mayer, Wilsonville, OR (US); James E. Van't Slot, Seattle, WA (US); Daniel Rawlings, Issaquah, WA (US)

(73) Assignee: Ingersoll-Rand Company, Bridgeton, MO (US)

( * ) Notice: Subject to any disclaimer, the term of this patent is extended or adjusted under 35 U.S.C. 154(b) by 0 days.

(21) Appl. No.: 09/759,890

(22) Filed: Jan. 12, 2001

(65) Prior Publication Data

US 2002/0116155 A1 Aug. 22, 2002

(Under 37 CFR 1.47)

(51) Int. Cl.[7] .......................... G06F 11/32; G01K 13/00
(52) U.S. Cl. ................... 702/188; 702/182; 702/132; 62/129
(58) Field of Search .................. 702/99, 132, 182, 702/188, 58, 57, 183, 189, 130; 340/286.09, 585, 588; 62/126, 127, 128, 129, 130, 131

(56) References Cited

U.S. PATENT DOCUMENTS

| | | | |
|---|---|---|---|
| 3,707,851 A | 1/1973 | McAshan, Jr. ............... 62/125 |
| 3,911,746 A | 10/1975 | Spangler et al. ........... 73/343.5 |
| 4,234,926 A | 11/1980 | Wallace et al. ............. 364/551 |
| 4,387,578 A | 6/1983 | Paddock ...................... 62/127 |
| 4,490,986 A | * | 1/1985 | Paddock ...................... 62/127 |
| 4,538,419 A | 9/1985 | Lord ........................... 62/129 |
| 4,630,449 A | 12/1986 | Adams ........................ 62/130 |
| 4,882,564 A | 11/1989 | Monroe et al. ............. 340/449 |
| 5,262,758 A | 11/1993 | Nam et al. ................... 340/588 |
| 5,287,294 A | 2/1994 | Baert et al. ................. 364/557 |
| 5,424,720 A | 6/1995 | Kirkpatrick ................. 340/585 |
| 5,460,006 A | * | 10/1995 | Torimitsu .................... 62/127 |
| 5,739,760 A | * | 4/1998 | Hatakeyama .............. 340/3.32 |
| 5,768,632 A | * | 6/1998 | Husted et al. ................. 710/72 |
| 5,775,809 A | 7/1998 | Cooley et al. .............. 374/164 |
| 5,878,377 A | * | 3/1999 | Hamilton, II et al. ....... 702/132 |
| 5,900,801 A | 5/1999 | Heagle et al. ......... 340/286.09 |
| 5,939,974 A | * | 8/1999 | Heagle et al. ......... 340/286.09 |
| 6,042,264 A | 3/2000 | Prusik et al. ................ 374/106 |
| 6,088,688 A | 7/2000 | Crooks et al. ............... 705/412 |
| 6,119,471 A | * | 9/2000 | Tanaka et al. ................ 62/130 |
| 6,378,315 B1 | * | 4/2002 | Gelber et al. ................. 62/80 |
| 6,411,916 B1 | * | 6/2002 | Pellerin ...................... 702/130 |
| 6,453,687 B2 | * | 9/2002 | Sharood et al. .............. 62/127 |
| 6,526,766 B1 | * | 3/2003 | Hiraoka et al. ............... 62/125 |
| 2001/0045096 A1 | * | 11/2001 | Tatter .......................... 62/129 |

* cited by examiner

Primary Examiner—Marc S. Hoff
Assistant Examiner—Jeffrey R. West
(74) Attorney, Agent, or Firm—Michael Best & Friedrich LLP (57) ABSTRACT A system for monitoring conditions relating to the status of items such as perishable food products stored in enclosed spaces has a number of sensors mounted in the spaces. Tables maintained by the system hold a description of the spaces to be monitored and the location and identity of the sensors within each space. The values detected by each sensor are periodically recorded and tested against benchmark values established for the stored items adjacent to the sensor. Values outside of the benchmark values create an alarm condition, and a set of alarm messages are displayed on a display unit. The alarm messages include suggested corrective actions. The user has the opportunity to signal to the system the corrective actions taken, and the system stores a record of these corrective actions in association with the corrective actions and the alarm condition.

3 Claims, 7 Drawing Sheets

SAMPLE HIGHLIGHTED SYSTEM TREE MAP

Fig. 5

ENVIRONMENTAL MONITORING SYSTEM

BACKGROUND OF THE INVENTION

Environments for spaces of many types must be accurately controlled. For example, it is routine to control temperature and humidity in occupied spaces. The environment within spaces used for storing or manufacturing products and apparatus of many types often must be controlled as well. For example, storage or manufacturing areas for electronic equipment often have temperature, dust and chemical contaminants, and humidity limits that must be closely observed. Over the years, a variety of reliable and effective control systems have been developed for meeting these requirements. However, for a variety of reasons these control systems sometimes fail, requiring human intervention. Further, it is often necessary to provide an historical record of these failures and also of proper operation.

For example, heating plants and air conditioners can fail because of a tripping circuit breaker, a short outage of fuel or electricity, or failure of a critical part of the system. In some cases these failures are nuisances only. In others, they may cause significant economic loss or may even threaten life or health of animals or humans. Consider the problem of controlling laboratory animals' environment. After a period of time, an experimenter may have a significant investment of time and money in ongoing experiments that will be lost if prescribed environmental conditions for the animals are not maintained. These laboratories may not be staffed around the clock, so that a defect in the space's environment may not be noticed for a period of many hours.

An even more important situation is controlling the environment in which food is stored. The need for food to have safe levels of various pathogens and contaminants can hardly be overstated. Anyone who has visited a modern supermarket knows of the sophisticated environmental controls for temperature and sometimes humidity as well, in produce displays. Yet these are nothing more than mechanical and electrical systems having large numbers of critical components, any of which are liable to failure. Although infrequent, failures can occur that affect the quality of the food. Refrigeration failures that persist for several hours are extremely costly, in that the food spoils and must be thrown out. Even worse, if the failure is intermittent the food may spoil in a way not readily noticeable, but that results in unhealthy food. For example, in a variety of inadequately refrigerated food products, *E. coli* and salmonella bacteria can grow to a level that may be harmful and yet leave no visual indication this has even happened. Even if the cooling and heating systems operate properly, improper loading of storage spaces, doors that don't close properly, operator error, etc. can affect food safety and quality.

The system to be described in this patent application has been developed primarily to monitor the temperature environment for perishable foods, but the principles can be easily extended to other types of things and creatures as well. Experts generally regard perishable food produce held at a temperature above 41° F. (5° C.) for more than 4 hours total as unsafe to eat. Dangerous pathogens will not usually proliferate in food that is held between 38 and 41° F. (4° C.) but quality may be affected by spoilage, wilting, etc. So the standard for safe storage of perishable food products now sets 33–38° F. (0.5–4° C.) as the proper range for storage of these materials.

The federal Food and Drug Administration (FDA) and the Department of Agriculture (DA) are in the process of setting standards for storing fresh perishable foods. These standards are defined by rules identified by the acronym HAACP (Hazard Analysis of Critical Control Points). HAACP is currently under modification, but essentially specifies a set of required activities for food storage. These activities include:

- specifying temperature limits for various types of food products
- monitoring temperature of food products having temperature limits
- notifying an operator when limits are exceeded
- correcting the problem when temperature limits are exceeded to assure safety
- documenting the preceding activities, and
- verifying all of the preceding activities At the present time, operators of food storage and marketing facilities perform these steps manually. Thermometers are placed in food display cases, and are periodically read and recorded manually. The people in charge of the facility take what seems to be the appropriate actions whenever a temperature is read as out of the stated limit, and then document and verify the corrective action.

This approach has a number of disadvantages. It is labor-intensive and therefore expensive. Since most of the time there is no problem, it is easy to lose the discipline needed to make the readings at the scheduled times. Since humans are involved, it is likely that the sensors will not be read as scheduled or will be read incorrectly. Manual reading cannot be done frequently enough to avoid loss of food quality or even pathogen growth when out of range temperatures occur. The corrective actions taken may not immediately correct the problem. For example, a corrective action of reducing the set point temperature will not easily solve the failure if the reason the temperature has risen above the limit because the case is overfilled or a cold air duct is obstructed. Manual readings may not detect brief temperature excursions past the limit, say those caused by defrosting. On the other hand, when manual readings do detect these excursions the response may be to take unneeded corrective actions.

Where sensors are not visible from outside the display case and must be read with the door open, further error in the readings may result. All of these conditions can result in erroneous monitoring of the conditions within food storage spaces.

Of course, similar considerations are present for freezer cases and hot food cases. In fact, hot food cases have the potential for very rapid pathogen growth if the temperature falls much below a safety temperature.

The result of all these considerations is that monitoring the storage environment generally and the temperature in particular for various foods is a difficult and expensive activity that may often result in inaccurate detection of food condition. If healthful food is detected as bad, this leads to unnecessary discarding of food and substantial unnecessary expense. If bad food is detected as good, this may give rise to a serious health issue, with enormous consequences both for consumers and the businesses in the food supply chain.

Accordingly, an alternative to manual sensor monitoring is advantageous. There have been systems described in the past that provide alternatives to manual monitoring. Among these, U.S. Pat. Nos. 5,900,801 and 5,939,974 (both to Heagle et al.) teach a comprehensive system for monitoring food preparation, storage, and delivery. A number of patents described in the Heagle patents also disclose environmental monitoring systems.

BRIEF DESCRIPTION OF THE INVENTION

We have developed a system for monitoring a varying and measurable parameter level at a plurality of points within a space. We expect that the users will usually chose to monitor the quality or condition of products stored in the space. We intend the term "product" to include a wide variety of goods, food products, and material whose quality or condition is affected by some parameter or condition of the product's environment such as temperature, humidity and moisture content, vibration, airborne contamination, microbial contamination, etc. The application we presently prefer for the system is to monitor the temperature within food storage spaces.

This system includes a plurality of product condition sensors each having an associated identifier code. Each sensor is to be placed in physical proximity to a product so as to measure the product condition parameter level. Each sensor provides a sensor signal encoding the measured parameter level.

We find it convenient to use a small computer along with appropriate software and some sort of interface for communicating with the sensors to provide the remaining elements of the invention.

The computer conveniently provides a memory as a further element of the system. The memory is first, for recording at least one predetermined parameter value in association with each sensor identifier code, and second, for recording in association with each predetermined parameter value, a set of message code strings for a plurality of messages. These message code strings encode printable messages providing status information or suggesting remedial action for a user when an out-of-range condition is detected for the condition sensed by the sensor. Thirdly, the memory records application software whose execution causes the computer to provide the desired functionality of the invention.

The computer's display component functions as a display unit in this invention for providing a visual display of messages responsive to a display signal encoding the set of message code strings.

When the computer executes the application software recorded in the memory, it becomes physically and functionally a data analyzer. The computer/data analyzer element receives the sensor signal from a sensor and a predetermined parameter value recorded in the memory in association with that sensor's identifier code. The data analyzer then compares the measured parameter value encoded in the sensor signal with the received parameter value associated with the sensor's identifier code. Responsive to a predetermined relationship between the measured and recorded parameter levels, the data analyzer retrieves from the memory the set of message code strings associated with the recorded parameter value, and encodes the retrieved set of message code strings in a display signal provided to the display unit.

DESCRIPTION OF THE PREFERRED EMBODIMENTS

The system shown in these Figures is designed to monitor and report temperature excursions within a controlled environment space outside a predetermined temperature range. In some instances, the range may be defined at only one end, as when the low temperature is immaterial and it is only necessary to detect temperature excursions where growth of pathogens is possible. The range may also be defined at both ends, say when freezing of refrigerated produce will affect quality, and where temperatures above 41° F. can cause pathogen growth.

Figure 1:
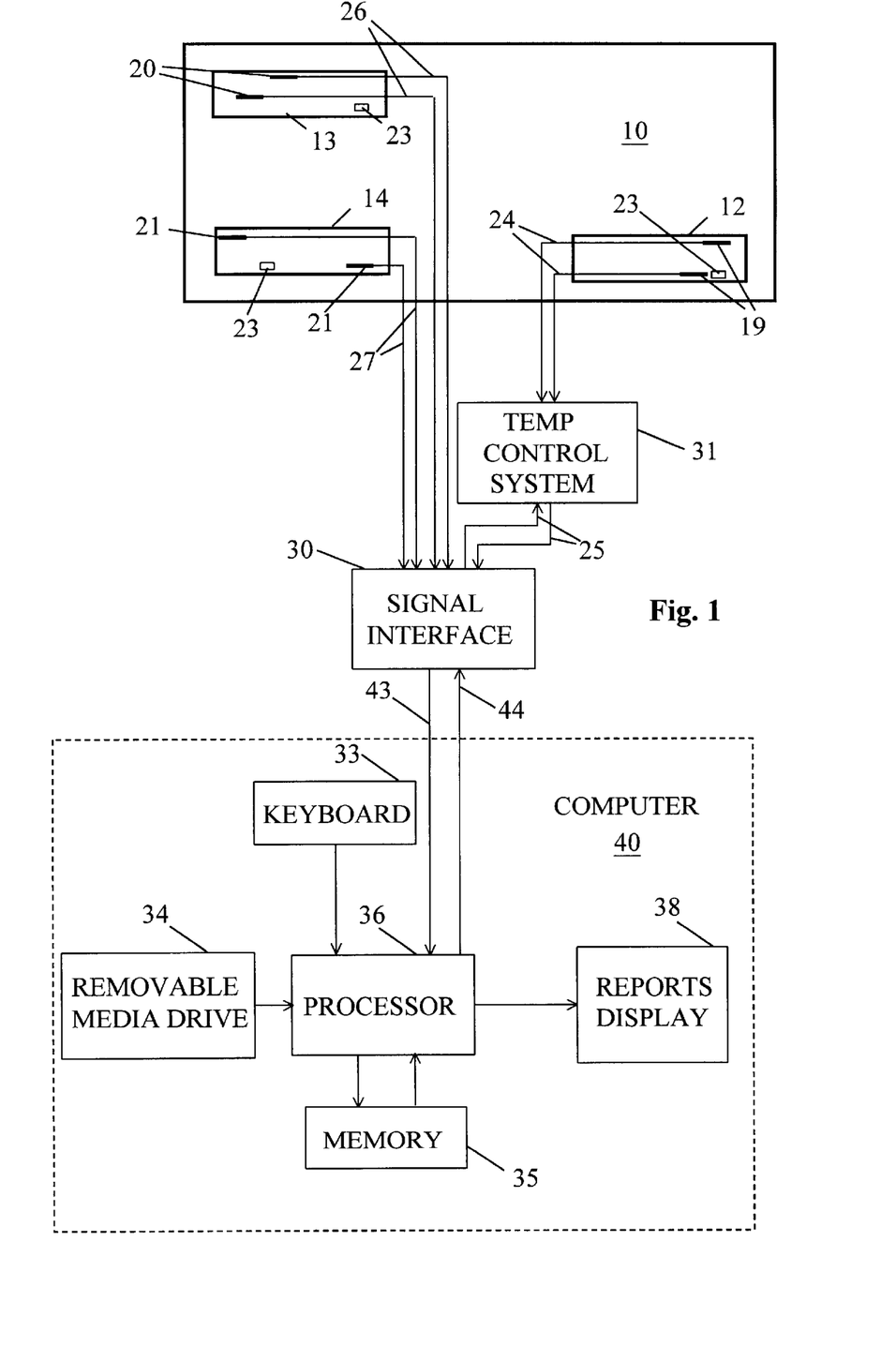
FIG. 1 is a diagram of a system including a number of controlled spaces within a facility and a computer system incorporating the invention for monitoring temperature within the controlled spaces.

In FIG. 1 a facility or enclosure 10 has a number of controlled environment spaces 12, 13, 14 for storage of perishable or other types of items whose temperature should be kept cooled to within a specified range. The facility 10 may be a food storage area such as a supermarket and the environment spaces 12–14 may be refrigerated or heated display cases within facility 10. As explained above, food safety and quality requires storage spaces for perishable food to be held within predetermined temperature ranges. Even if the product is not a perishable, such as a bottled beverage, holding it within some temperature range may still be desirable to enhance the salability of the product. In such situations, freezing a bottled or canned product can damage or destroy its salability. In FIG. 1, a refrigeration or heating system, a part of which is shown as temp control system 31, controls temperature within each of the spaces 12–14.

As an example, each of the spaces 12–14 has within itself, two product condition sensors 19, 20, or 21 respectively, although the number of sensors is not important to this invention. Each of the sensors 19–21 detects a temperature indicative of the temperature of adjacent products 23 stored in the space 12–14 involved. The sensors 19–21 are located in sufficient physical proximity to products 23 to allow temperatures of these products to be sensed. The sensors 19 are shown as connected through data paths 24 to temp control system 31 for purposes of controlling temperature within space 12. The temperature value sensed by each sensor 19–21 is encoded in a sensor signal on one of the data paths 25, 26, or 27 respectively and provided to a signal interface 30. The data paths 25 are connected between system 31 and interface 30, with one of the paths carrying requests to system 31 and the other to carry the actual sensor signals. The type of individual sensors 19–21 as well as their placement within the spaces 12–14 is well known in to those familiar with storage of food products and other items requiring a temperature-controlled environment. Suffice it to say that the placement and number of sensors 19–21 should allow the sensor to provide an accurate indication of the temperature of adjacent products.

Our present embodiment can operate with four types of sensors: those that directly sense ambient air temperature, those mounted within objects simulating the stored products and indicating the temperature within the simulated products, those inserted within stored products, and those such as sensors 19 that form a part of another system such as the temperature control or refrigeration system. Such sensors are well known in food storage technology. The system can also operate with other types of sensors.

Signal interface 30 is some sort of multiplexer that receives the individual sensor signals on paths 25–27 and provides the data encoded in the individual sensor signals on path 43. A control or address signal on path 44 designates or gates one of the sensor signals from the paths 25–27 to path 43. In some cases, the sensor signals carried on path 43 are provided to temperature control software concurrently operating within computer 40 and are not directly accessible to the invention's software within computer 40. In that case, the software of this invention simply requests the sensor signal value from the appropriate software. This too is well known in control and signal processing, and no further notice need be taken of it.

Computer 40 includes a standard processor or CPU 36 found in every personal computer. Processor 36 communicates with a memory 35 for storing data and software and executes the software held in memory 35. Memory 35 will usually be an internal disk drive having media surfaces on which data is recorded. Processor 36 provides display signals in the conventional way to a reports display 38 comprised of a conventional CRT or LCD display unit on which humans can read messages formed from individual character strings encoded in the display signals. A keyboard 33 allows an operator to provide data and messages to processor 36. A removable media drive 34, typically a CD ROM or floppy disk, allows software and data to be loaded into memory 35.

Figure 2:
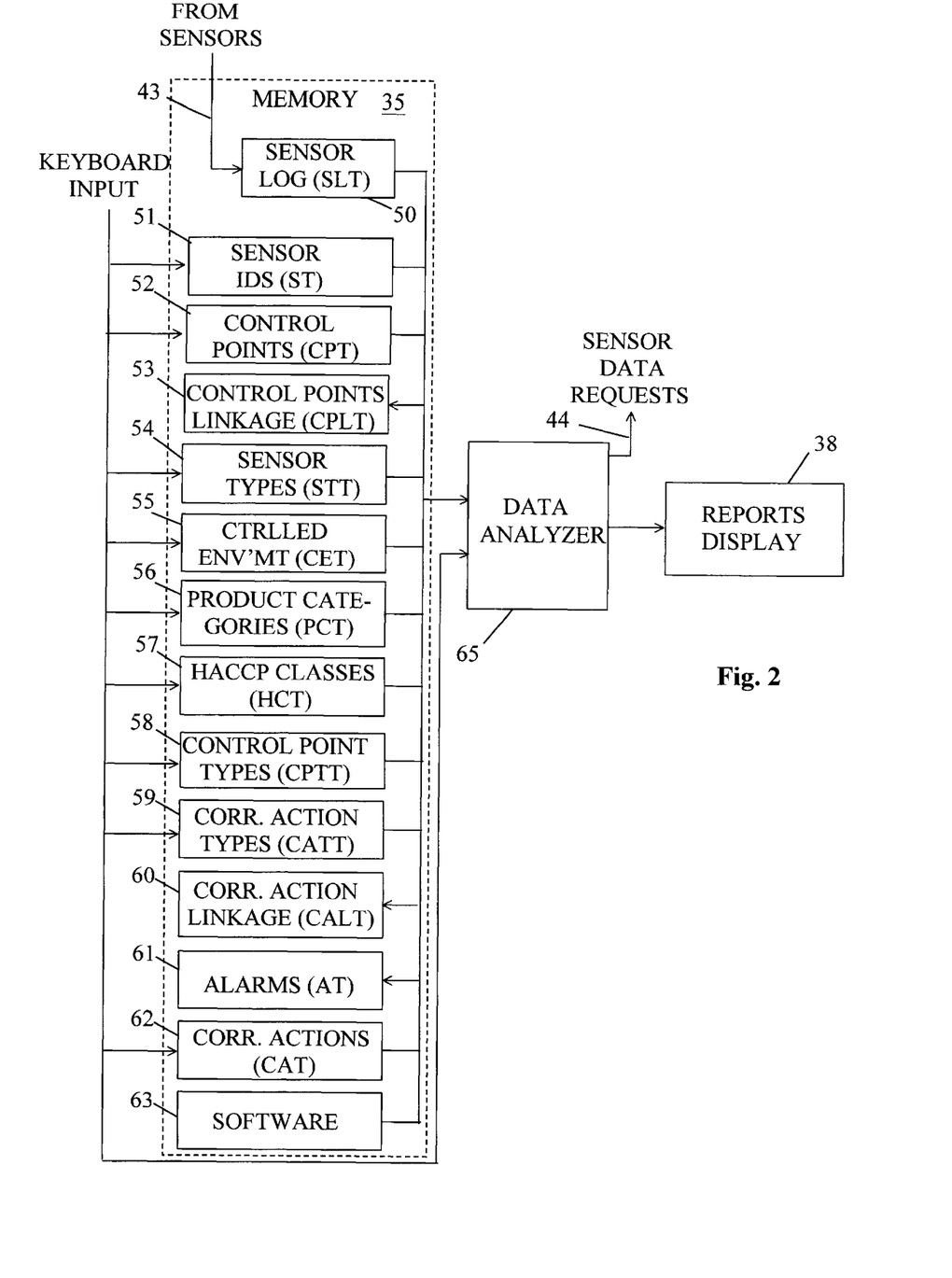
FIG. 2 is a block diagram of the computer of FIG. 1 generally showing the various functional elements of the invention provided by the computer.

FIG. 2 shows the invention in more detail. The invention is for the most part incorporated in the software that executes in processor 36 and is shown as a storage element 63 within memory 35, and in the data held by a number of data table modules 50–62 forming a part of memory 35. Large parts of tables 51–62 are typically loaded into memory 35 through drive 34 as a part of the system, but may also be modified for a particular facility by data entry using keyboard 33. The data held by tables 50–62 is processed by a data analyzer 65 formed by execution by processor 36 of the software of the invention. The outputs of the data analyzer 65 are reports displayed on display 38, and shown in FIG. 2 as reports display 38. The tables 50–62 and the software module 63 all have actual physical existence within memory 35, in that physical portions of the medium forming memory 35 record these tables and object code.

Figure 3A:
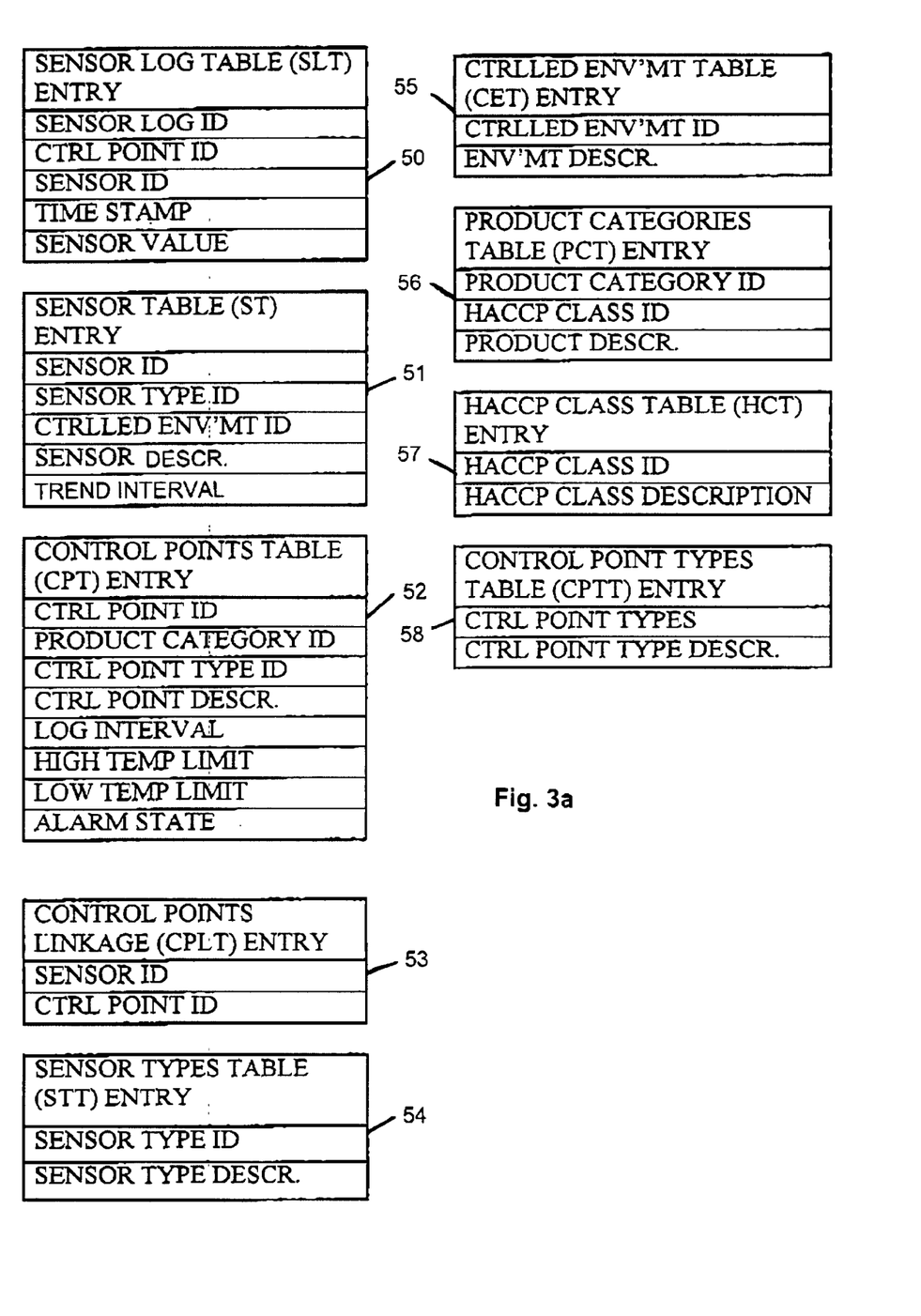
FIGS. 3a and 3b show the important structural elements of the tables maintained by the computer of FIG. 2 in implementing the invention.
Figure 3B:
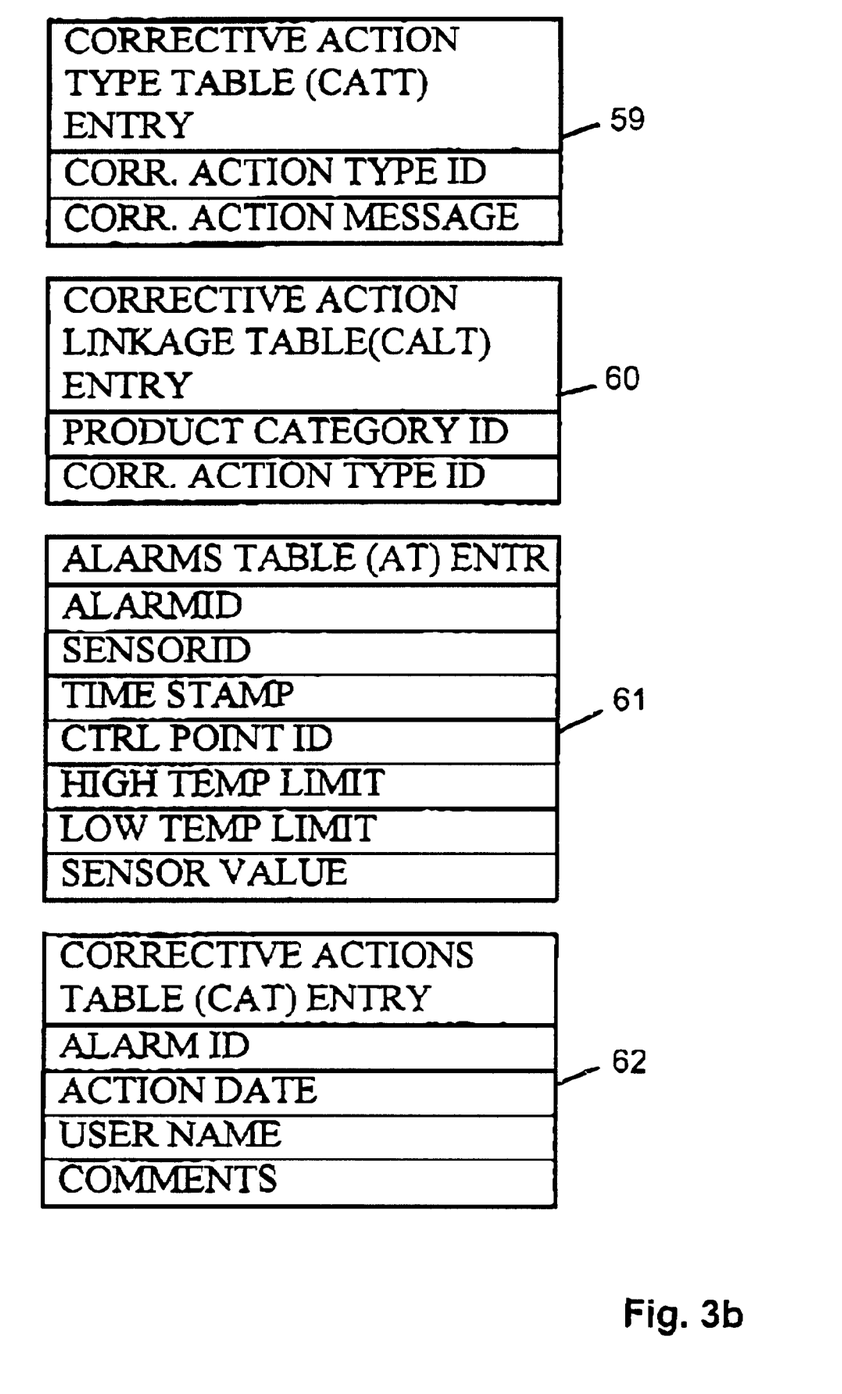

The format of an entry for each of the tables 50–62 is shown in FIGS. 3a and 3b. Each of the tables 50–62 comprises two or more entries of the format shown, and each entry comprises two or more fields. The number of entries for a table and the size of an individual field within a particular table's entry should be selected to hold the expected amount of data, and these selections, while not trivial, are well known considerations and well within the ability of typical programmers. Most of the tables have as the leftmost field of their entries, an ID value that is different within that table for each entry, and by which that entry may be identified and accessed.

The purpose of each table is best defined by the types of information its fields hold. It is easiest to use a tabular form to define the information held by individual fields within table entries. The use of field names is consistent throughout FIGS. 3a and 3b and in the description of the FIGS. 4a and 4b flowcharts, so explaining or defining the contents of a field one time will suffice for the remainder of this description. For convenience, abbreviations for table names are shown parenthetically in FIGS. 2, 3a and 3b, and these will be used in the definitions below as well as in the flowcharts of FIGS. 4a and 4b. Rather than organizing the definitions alphabetically, they are in the order they first appear in FIGS. 3a and 3b.

FIELD DEFINITIONS FOR TABLES

SENSOR LOG ID Uniquely specifies each entry of the SLT.

CTRL POINT ID Uniquely specifies each entry of the CPT.

SENSOR ID Uniquely specifies each entry of the ST.

TIME STAMP Holds the precise time and date at which the entry was created.

SENSOR VALUE Holds the value provided by the sensor defined by the SENSOR ID field at the time held in the TIME STAMP field.

SENSOR TYPE ID Uniquely specifies each entry of the STT.

CTRLLED ENV'MT ID Uniquely specifies each entry of the CET.

SENSOR DESCR. Message code string describing the sensor by a variety of factors such as location.

TREND INTERVAL The time interval over which sensor temperature (SENSOR VALUE) changes are tracked to sense excessive rate of temperature change.

PRODUCT CATEGORY ID Uniquely specifies each entry of the PCT.

CTRL POINT TYPE ID Uniquely specifies each entry of the CPTT.

CTRL POINT DESCR. Message code string describing the control point.

LOG INTERVAL The time interval between successive testing of the sensor values associated with the control point against the control point's temperature range.

HIGH TEMP LIMIT/LOW TEMP LIMIT The two temperature values that define the control point's temperature range and serve as benchmark values. It is entirely possible for two or more CPT entries to associate the same sensors' values with different temperature ranges, and in fact this is the expected situation.

ALARM STATE Indicates whether one or more of the sensor values associated with the control point are out of range at the particular time.

SENSOR TYPE DESCR. Message code string describing the sensor by a variety of factors such as location.

ENV'MT DESCR. Message code string describing the environment identified by the CTRLLED ENV'MT ID field by location and type of product stored. The contents of this table can be expanded into two or more other tables as well.

HACCP CLASS ID Message code string specifying the HACCP class for the products identified by the PRODUCT CATEGORY ID field.

HACCP CLASS DESCR. Message code string specifying the HACCP class for the products identified by the PRODUCT CATEGORY ID field.

CTRL POINT TYPE DESCR. Message code string describing the control point type, such one providing food safety or quality monitoring.

CORR. ACTION TYPE ID Uniquely specifies each entry of the CATT.

CORR. ACTION MESSAGE Message code string describing one or more corrective actions, such closing a refrigerated case's door, resetting the thermostat, checking the refrigeration unit's circuit breaker, etc.

ALARM ID Uniquely specifies each entry of the AT.

TIME STAMP Holds the precise time and date at which the entry was created. This value should be equal to or nearly equal to the TIME STAMP field of the corresponding SLT entry.

ACTION DATE specifies the time when a particular corrective action was taken.

USER NAME specifies the person identified as taking the corrective action.

It is also helpful to discuss certain of the tables shown in FIG. 2. CPLT entry links a sensor through the SENSOR ID field to a single control point through the CTRL POINT ID field. In this way one of the sensors 19–21 can link to one or more control points, and one or more sensors 19–21 can link to a single control point. In practical terms this means that two or more temperature ranges can be applied to a single one of the sensors 19–21.

The CPT may well have two or more entries with the same SENSOR ID, each of these entries having a different temperature range. In this way the same sensor 19–21 may be monitored for two different temperature ranges. In food storage as was explained earlier, the temperature for food safety is frequently different from that for food quality. We expect that the CPT entries will typically assign two temperature ranges to each sensor 19–21. Thus, food products 23 whose temperature is measured by a sensor 19–21 will have two different temperature ranges that may generate alarms, one assigned to or sensing quality of the food, the other safety.

Each CALT entry links a product category as defined in the PCT with one or more corrective actions as defined in the CATT. This allows a single set of corrective actions to be applied to a number of different product categories. If at some later time requirements for safe food storage change, it is easy to change the corrective actions for all of the associated product categories.

Each AT entry holds details of every out of range incident sufficient to allow all of the parameters of the event to be recreated. The individual AT entries will not normally be changed after creation.

Lastly, it is convenient to simply refer to the value stored in an entry's field by the name of that field, and this convention will be followed in the following text unless the context or an explicit statement to the contrary indicates the opposite.

Figure 4A:
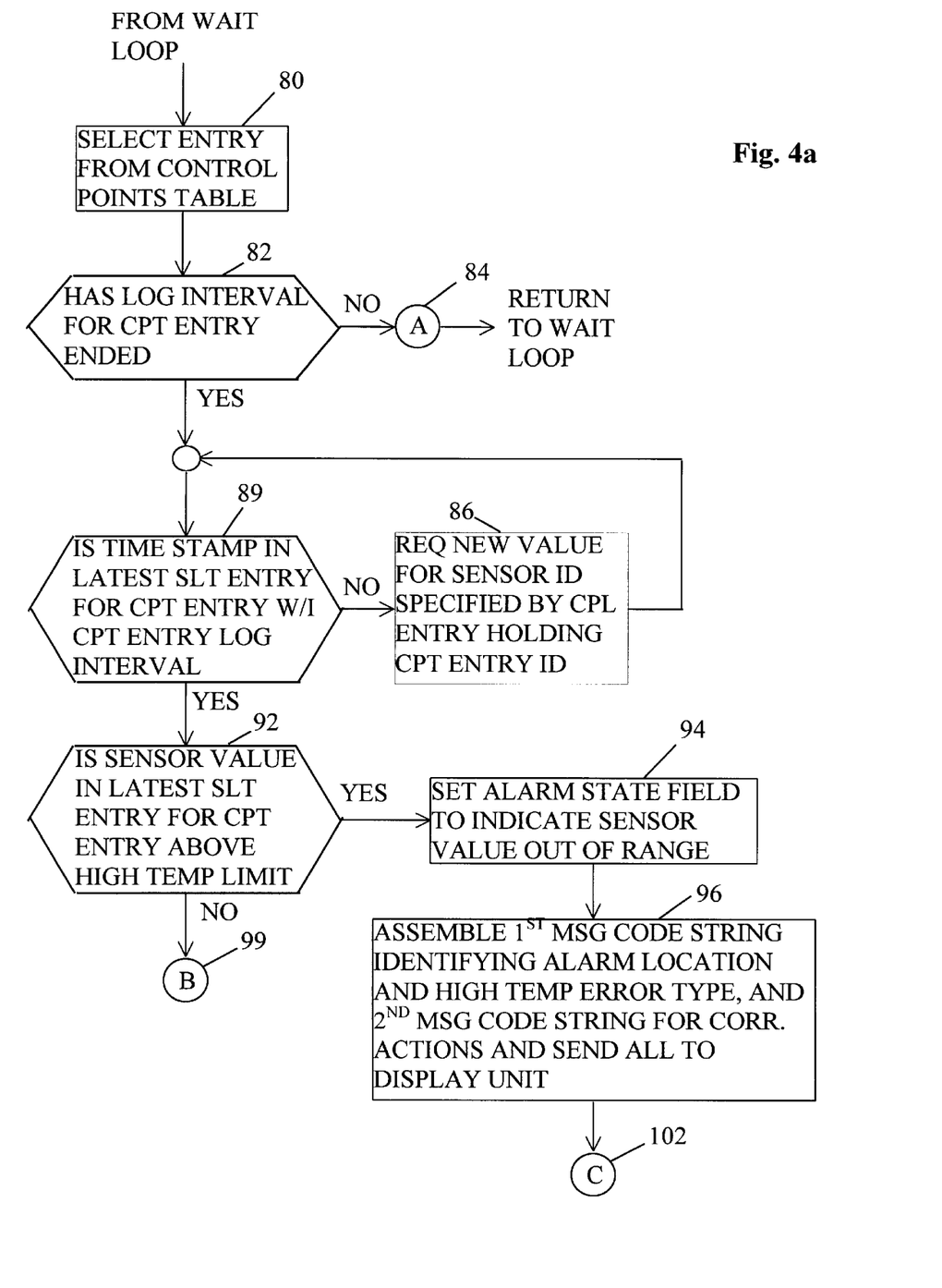
FIGS. 4a and 4b are a flowchart of software whose execution by the computer of creates elements of the invention.
Figure 4B:
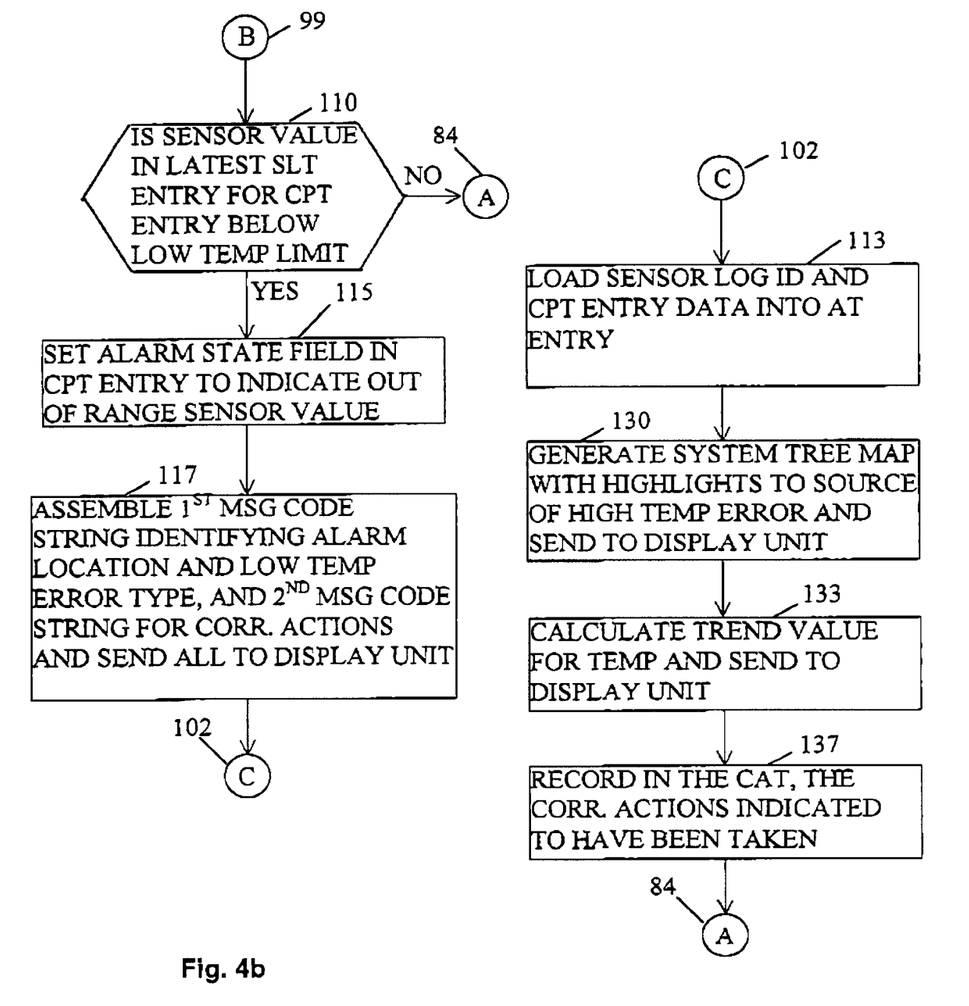

With an understanding of the tables used and formed by the software of this invention, turn to FIGS. 4a and 4b. Processing starts in a wait loop that periodically cycles through all of the entries in the CPT. By linking two or more CPT entries with different temperature ranges to a single one of the sensors 19–21 through the CPLT, it is possible to produce alarms for a single sensor for two or more temperature ranges.

The flowcharts in FIGS. 4a and 4b describe the structure of software instructions whose execution causes the processor 36 to become the data analyzer 65 and to implement the invention. Those familiar with in the software arts realize that first, software has a specific physical existence within the processor that executes the software, and second, that the processor itself becomes a functional element performing the programmed function while executing the software. As to the first point, the software memory 63 (FIG. 2) has a physical structure that incorporates the unique combination of software instructions loaded into and readable from the memory and thereby uniquely defines its own structure. As to the second point, while the data processor is executing the instructions for any particular function, the processor becomes for that short period of time a physical functional element executing that function. As instruction execution continues, the processor successively becomes the physical embodiment of each of the functional elements intended by the programmer. As a set of instructions for a particular function is re-executed, the processor can become that functional element as many times as is required. From this standpoint one can easily realize that a properly programmed processor is a physical device in which an invention can easily be implemented. A processor implementation of an invention is often preferred to discrete or special purpose hardware because of cost savings to produce, relatively easy development, and ease of modification and upgrade.

It is useful to generally discuss the flowcharts of FIGS. 4a and 4b and the three types of symbol boxes in them. These flowcharts describe the functions of software stored in software memory 63 of FIG. 2 and which implements the various functions of the invention. Each symbol box represents one or more processor 36 instructions. The text within the box briefly describes the functions performed by executing the instructions symbolized by that box. The lines with arrows connecting the boxes signify the order in which the instructions symbolized by the boxes are to be executed, with the flow of instruction execution following the direction of the arrowheads. Rectangular boxes such as element 80 of FIG. 4a are activity elements indicating some type of computational activity, the term "computation" being used here in its broadest sense.

Hexagonal boxes as at 82 of FIG. 4a are decision elements and have two paths labeled "YES" and "NO" from them to (most often) two further symbol boxes. Decision element instructions test some mathematical or logical characteristic or condition. Depending on the test result, instruction execution can either continue in sequence or take a path to another symbol box specified by the results of that test. A decision element also symbolizes one or more processor 36 instructions testing the specified condition or arithmetic or logical value and causing instruction execution to branch depending on the result of that test. Lastly, circles comprising connector elements as at 84 of FIG. 4a specify that instruction execution continues at another point in the instruction sequence without direct connection between them by lines with arrows. The letter in the circle designates the connector element at which instruction execution is to continue.

As explained above, the instructions that an activity or decision element symbolizes cause the processor to become during execution of those instructions, the functional equivalent of a physical device that performs the stated function. Of course each functional element exists for only a short time, and during this time none of the other elements exist. However, nothing in the patent law requires all of the components of an embodiment described in a patent to simultaneously exist. Accordingly, one can describe and claim the invention using terms describing these physical devices in terms of their software equivalents.

Note there may be many different specific embodiments of these physical devices that the data processor that all provide identical functionality. We wish to include all of these possible different embodiments in the definition of our invention, and do not wish to limit ourselves to the single one shown in the flowcharts of FIGS. 4a and 4b. In particular, the description of the invention is based on a specific organization of the tables 50–62. It goes without saying that the tables can be structured in a variety of ways and still provide all or most of the invention's functionality.

In FIG. 4a, processing starts with execution transferring to the instructions of element 80 from a wait loop. The wait loop allows processor 36 to execute instructions for software applications sharing processor time with the invention's software. Element 80 modifies a pointer or index that designates the CTRL POINT ID for the next CPT entry. Then the instructions of decision element 82 tests whether the LOG INTERVAL field time has elapsed since the last time the CPT entry was selected. If not, instruction execution transfers back to the wait loop through connector element A 84, and if so, the instructions of decision element 89 are executed next. By constantly returning to element 80, the temperature sensed by a single sensor 19–21 can be associated with two or more temperature ranges.

The instructions of decision element 89 first select the sensor associated with the selected CPT entry by finding the CPLT entry holding the selected CPT entry's CTRL POINT ID. The SENSOR ID value in that CPLT entry will be called the linked SENSOR ID value. The instructions of element 89 then search for the most recent entry in the SLT with a SENSOR ID field equal to the linked SENSOR ID field. If there is no such SLT entry, or if that SLT entry has a TIME STAMP value that does not fall within the selected CPT entry's LOG INTERVAL field, then the instructions of element 86 are executed next. The instructions of element 86 first request on path 44 the current value from the sensor with the linked SENSOR ID value and receive that current value on path 43. The instructions of element 86 then form a new SLT entry by filling in all of the fields for an SLT entry shown in FIG. 3a and using the sensor value received on path 43 for the SENSOR VALUE of the new SLT entry, and then store that new SLT entry in the SLT. Then the instructions of decision element 89 are executed again.

At this point, there should be an entry in the SLT having the linked SENSOR ID value, so the instructions of decision element 92 are executed next. The instructions of element 92 test the sensor value recorded in the SENSOR VALUE field of the most recent SLT entry having the linked SENSOR ID value to fall above the HIGH TEMP LIMIT value in the selected CPT entry. If true, an out of range condition has been detected, and the instructions of element 94 are executed next. The instructions of element 94 cause the ALARM STATE field in the selected CPT entry to indicate that condition.

Then the instructions of element 96 assembles a first message code string that provides information about the alarm including the identity of the sensor 19–21 causing the alarm, and a second message code string that suggests corrective actions. The two message code strings are then encoded in a display signal and sent to display 38. The first message code string may include some or all of the following:

CTRL POINT DESCR. field of the selected CPT entry
SENSOR DESCR. field in the ST entry having the linked SENSOR ID value
SENSOR TYPE DESCR. field in the STT entry having the SENSOR TYPE ID value held in the ST entry having the linked SENSOR ID value
PRODUCT DESCR. field in the PCT entry having the PRODUCT CATEGORY ID value in the selected CPT entry
HACCP CLASS DESCR. in the HCT entry having the HACCP CLASS ID held in the PCT entry linked to the PRODUCT CATEGORY ID field in the selected CPT entry The second message code string has the suggested corrective actions. As mentioned earlier, the CALT links a PRODUCT CATEGORY ID with a CORR. ACTION TYPE ID field in the CATT. The second message code string comprises the CORR. ACTION MESSAGE in the linked CATT entry. Instruction processing then continues with element 113 in FIG. 4b through connector element C 102.

Returning to element 92 on FIG. 4a, if the sensor value is below the upper limit, then the instruction execution proceeds through connector element B 99 to decision element 110 on FIG. 4b. Element 110 tests whether the current value for the sensor linked by the CPLT entry to the selected CPT entry is less than the LOW TEMP LIMIT value in the selected CPT entry. If not, instruction execution returns to the wait loop through connector element A 84. If so, then an alarm exists, and activity element 115 is executed. Elements 115 and 117 correspond closely to elements 94 and 96 of FIG. 4a, and need no further discussion. Instruction execution then transfers to activity element 113 through element 102.

Figure 5:
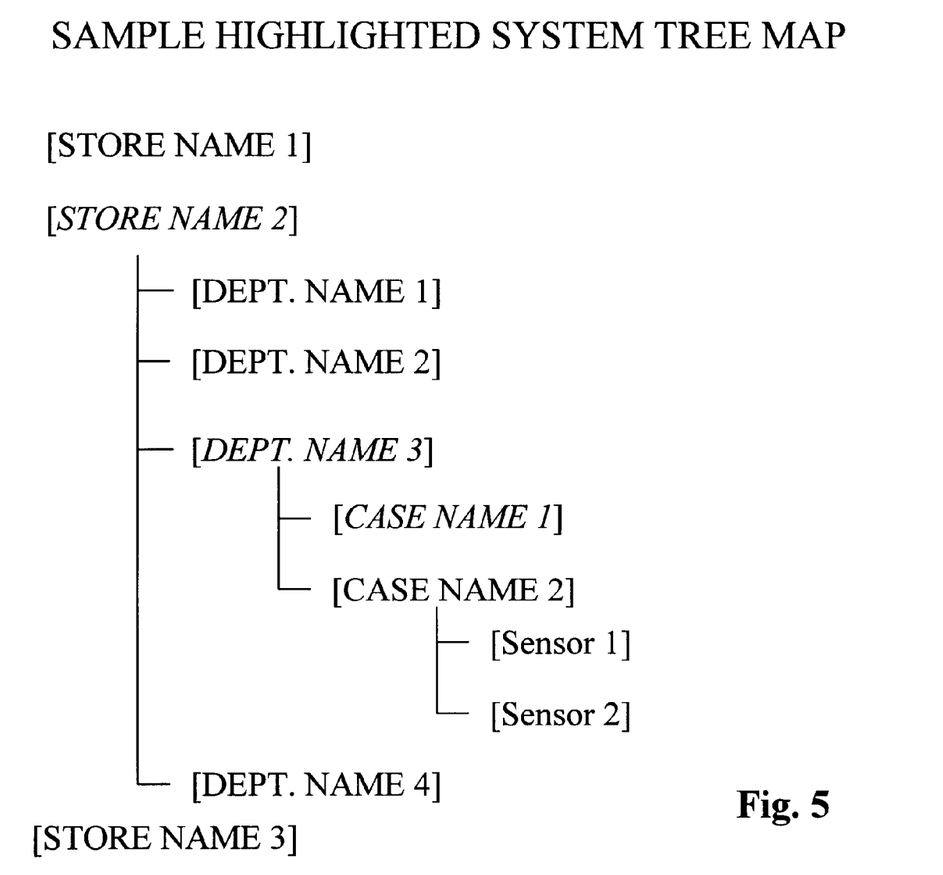
FIG. 5 shows a particular presentation of information by the invention.

Element 113 symbolizes instructions that assemble the data for a new AT entry. This data can include such information as the SENSOR LOG ID and the selected CPT entry data. Element 130 generates the highlighted system tree map that identifies visually which enclosed space has generated the alarm. A sample map is shown in FIG. 5. The italicized text would typically have a contrasting color on a color display unit 38.

Element 133 calculates a trend value indicating the rate at which the temperature sensed by the linked sensor has changed over the recent LOG INTERVAL times. This requires retrieving at least one recent temperature values for that sensor from the SLT entries having the linked SENSOR ID value. These temperatures are processed according to a predetermined algorithm to provide an algorithm value. The algorithm value is compared to a predetermined benchmark value. If the comparison reveals a predetermined relationship, a message code string is sent to the display 38 to provide an alarm.

In one embodiment, the SLT 50 records the current time at which each temperature is recorded. Element 133 functions as a temperature processing element, periodically retrieving all the temperatures recorded in the SLT 50 in association with one selected sensor within a trend interval value recorded in the ST 51. The trend interval ends with the current time. Element 133 instructions calculate the average of the temperatures so retrieved to create a moving average. The average temperature is compared with the HIGH LIMIT value in the CPT 52 entry currently selected, and if greater than that value, encodes the average temperature in a message code string and sends the string to the display unit 38 as a display signal.

Element 137 senses acknowledgement inputs from the keyboard 33 by a user that identify individual corrective actions and logs these in the CAT 62 with the ALARM ID value generated for the current alarm situation. Entries in the CAT will not normally be changed once formed, since they provide an audit trail indicating the environment for all of the control points held in the system. Element 137 functions as a communicator element that receives data encoded in a manual input signal from the keyboard 33. The manual input signal encodes a sender identity value and the identity of a particular corrective action. Element 137 also functions as a response logger element receiving the manual input signal and storing the sender identity value in association with an identifier of the associated corrective action.

As mentioned above, there are a wide range of methods for organizing and processing the data provided by the sensors 19–21, and that described here is only one possible preferred embodiment. Accordingly, we do not wish to limit ourselves to the detailed table structure or the specific software functions shown.

The preceding has described our invention, which we wish to protect by Letters Patent having these claims:

1. A system for monitoring in a plurality of controlled environment spaces, a varying and measurable parameter level indicating the condition of a plurality of products stored in the spaces, comprising:

a plurality of product condition sensors each having an associated identifier code, each sensor to be placed in physical proximity to at least one product and measuring a product condition parameter level, and providing a sensor signal encoding the measured parameter level;

a memory for recording 1) at least one predetermined parameter value in association with each sensor identifier code, and 2) a set of message code stings for a plurality of messages in association with each predetermined parameter value;

a display unit for providing a visual display of messages responsive to a display signal encoding the set of message code strings;

a data analyzer receiving the sensor signal from a sensor and a predetermined parameter value recorded in the memory in association with that sensor's identifier code, comparing the measured parameter value encoded in the sensor signal with a parameter value associated with the sensor's identifier code, and responsive to a predetermined relationship between the measured and recorded parameter levels, retrieving from the memory the set of message code strings associated with the recorded parameter value, and encoding the retrieved set of message code strings in a display signal provided to the display unit; and wherein the memory includes a space recording a control points table (CPT), a sensor table (ST), a controlled environment table (CET), and a control points linkage table (CPLT), each of said tables having a plurality of entries, wherein said CPT entries have fields recording a unique control point ID, a sensor ID, and a parameter value, ST entries have fields recording a unique sensor ID associated with a preselected sensor, and a controlled environment ID, CET entries have fields recording a unique controlled environment ID and a description message code string, and CPLT entries have fields recording a sensor ID and a control point ID, and wherein the data analyzer further includes a selector for retrieving the contents of a selected CPT entry, a sensor interface for receiving the sensor signal from the sensor whose sensor II) is in the CPLT entry, a comparator for comparing the value encoded in the sensor signal with the parameter value recorded in the CPT entry having the control point ID recorded in the selected CPLT entry, and a display generator for providing a display signal to the display unit encoding the message code string encoded in the GET entry whose unique controlled environment ID is recorded in the ST entry whose unique sensor ID is recorded in the selected CPLT entry.

2. The system of claim 1, wherein the CPT entries further include a product category ID field and wherein the memory further includes a space recording a corrective action type table (CATT) and a space recording a corrective action linkage table (CALT), each of said tables having a plurality of entries, wherein said CPT entries have a field recording a product category ID, CATT entries include a unique corrective action type ID and a corrective action message code sting, and CALT entries include a product category ID and a corrective action type ID, and wherein the display generator provides a display signal further encoding the corrective action message code string in the CATT entry whose corrective action type ID is recorded in a CALT entry having the product category ID in the selected CPT entry.

3. The system of claim 1, wherein the memory further includes a space recording a product categories table (PCT) having a plurality of entries each POT entry having a fields recording a unique product category ID and a product description message code string, and wherein the display generator further provides in a display signal the product message code string recorded in the POT entry in which is also recorded the product category ID recorded in the selected CPT entry.

* * * * *

UNITED STATES PATENT AND TRADEMARK OFFICE
CERTIFICATE OF CORRECTION

PATENT NO.    : 6,725,180 B2
DATED         : April 20, 2004
INVENTOR(S)   : John Mayer, James E. Van't Slot and Daniel Rawlings

It is certified that error appears in the above-identified patent and that said Letters Patent is hereby corrected as shown below:

Column 11,
Line 14, "stings" should be -- strings --.

Column 12
Line 7, "II)" should be -- ID --.
Line 15, "GET" should be -- CET --.
Line 27, "sting" should be -- string --.
Lines 37 and 41, "POT" should be -- PCT --.

Signed and Sealed this

Eighteenth Day of January, 2005

JON W. DUDAS
*Director of the United States Patent and Trademark Office*